United States Patent [19]
Goetz et al.

[11] Patent Number: 4,965,370
[45] Date of Patent: Oct. 23, 1990

[54] N-METHYL-2-PYRROLIDONE PURIFICATION

[75] Inventors: Kenneth D. Goetz; Bradley L. Munro, both of Bartlesville, Okla.

[73] Assignee: Phillips Friedman Company, Bartlesville, Okla.

[21] Appl. No.: 396,208

[22] Filed: Aug. 21, 1989

[51] Int. Cl.$^5$ ............... C07D 201/14; C07D 207/267
[52] U.S. Cl. ..................................................... 548/555
[58] Field of Search ....................................... 548/555

[56] References Cited

U.S. PATENT DOCUMENTS

| | | | |
|---|---|---|---|
| 3,130,108 | 12/1964 | Eckstrom et al. | 159/6 |
| 3,678,983 | 7/1972 | Widmer et al. | 159/6 W |
| 4,256,568 | 3/1981 | Schlosberg et al. | 208/263 |
| 4,501,902 | 2/1985 | Cleary | 548/555 |
| 4,510,316 | 4/1985 | Cleary et al. | 548/555 |

OTHER PUBLICATIONS

Luwa Corporation Bulletin, EV-24, "Luwa Thin Film Evaporation Technology".

*Primary Examiner*—David B. Springer
*Attorney, Agent, or Firm*—Kenneth D. Goetz

[57] ABSTRACT

A process for recovering N-methyl-2-pyrrolidone from an effluent stream in a poly(arylene sulfide) process containing N-methyl-2-pyrrolidone contaminated with acidic compounds and high boiling contaminants by contacting the kettle liquid from a heavies fractionation zone with an inorganic compound selected from the group consisting of alkaline earth oxides and alkaline earth hydroxides in an amount effective to reduce the acidic compound content of the kettle liquid, and introducing the treated kettle liquid into a thin film evaporation zone to produce an overhead product containing N-methyl-2-pyrrolidone and a bottoms stream containing N-methyl-2-pyrrolidone soluble reaction products of the acidic compounds with the inorganic compound, unreacted acidic compounds and high boiling contaminants. The thin film evaporation zone overhead product stream can be recycled to the heavies fractionation zone, or introduced to an N-methyl-2-pyrrolidone recovery zone and fractionated to produce an overhead product stream consisting essentially of N-methyl-2-pyrrolidone and an intermediate heavies bottoms stream. In a further embodiment, the N-methyl-2-pyrrolidone recovery zone overhead product can be recycled to the heavies fractionation zone.

29 Claims, 2 Drawing Sheets

N-METHYL-2-PYRROLIDONE PURIFICATION

BACKGROUND OF THE INVENTION

This invention relates to a process for treatment and recovery of N-methyl-2-pyrrolidone from an effluent stream in a poly(arylene sulfide) process. In a specific aspect, tho invention relates to a process for removing acidic compounds from N-methyl-2-pyrrolidone which utilizes a thin-film evaporator.

In processes for the recovery of N-methyl-2-pyrrolidone which is used in the production of poly(arylene sulfide), the final process step is the recovery of N-methyl-2-pyrrolidone contaminated with acidic compounds such as phenol, N-methylsuccinimide and dimethylpyrrolidone, and high boiling contaminants. It is desirable to keep acidic impurities in N-methyl-2-pyrrolidone used for poly(arylene sulfide) production to a minlmum since their presence, particularly phenol and N-methylsuccinimide, can upset the stoichiometry of the polymerization reaction and result in the formation of off-specification polymer. Under typical oparating conditions in a fractionation process, N-methyl-2-pyrrolidone will be produced which stil contains acidic impurities above the minimum acceptable level or the recovery of specification N-methyl-2-pyrrolidone will be lowered resulting in an uuacceptable loss of N-methyl-2-pyrrolidone.

In U.S. Pat. No. 4,501,902, incorporated herein by reference, there is disclosed a process wherein kettle liquid from an N-methyl-2-pyrrolidone recovery fractionation column containing N-methyl-2-pyrrolidone, acidic compounds and high boiling contaminants is treated with an inorganic compound for removal of acidic contaminants. While the process of U.S. Pat. No. 4,501,902 is an advancement in the art, the process of the invention is a significant improvement and solves a previously unrecognized problem by providing a process for removing the reaction products of the acidic compounds, particularly phenol, with the inorganic compound which are soluble in N-methyl-2-pyrrolidone. These soluble reaction products would foul a typical fractionation column for recovering N-methyl-2-pyrrolidone and result in frequent and costly maintenance, and unacceptable plant downtime.

SUMMARY OF THE INVENTION

It is an object of the invention to provide a process for recovering N-methyl-2-pyrrolidone from a poly-(arylene sulfide) process effluent stream containing N-methyl-2-pyrrolidone contaminated with acidic compounds and high boiling contaminant. It is a further object of the invention to provide a commercially viable process for recovering N-methyl-2-pyrrolidone which is capable of handling solids resulting from N-methyl-2-pyrrolidone soluble reaction products of acidic compounds with inorganic compound. It is a further object of the invention to recover N-methyl-2-pyrrolidone that can be recycled for further production of poly(arylene sulfide).

According to the invention, N-methyl-2-pyrrolidone is recovered from an effluent stream in a poly(arylene sulfide) process containing N-methyl-2-pyrrolidone contaminated with acidic compounds and high boiling contaminants by passing the effluent stream to a heavies fractionation zone and frsctionating the effluent stream to produce a first overhead product stream containing N-methyl-2-pyrrolidone and a kettle liquid containing the remaining N-methyl-2-pyrrolidone, acidic compounds and high boiling contaminants, contacting the kettle liquid wlth an inorganic compound selected from the group consisting of alkaline earth oxides and alkaline earth hydroxides in an amount effective to reduce the acidic compound content of the kettle liquid, and introducing the thus treated kettle liquid into a thin-film evaporation zone and evaporating to produce a second overhead product stream containing N-methyl-2-pyrrolidone and a bottoms stream containing reaction producis of the acidic compounds with the inorganic compounds which are soluble in N-methyl-2-pyrrolidone, unreacted acidic compounds, and high boiling contaminants. In one embodiment, the second overhead product stream is recycled to the heavles fractionation zone. In another embodiment, the second overhead product stream is introduced to an N-methyl-2-pyrrolidone recovery zone and fractionated to produce a third overhead product stream consisting essentially of N-methyl-2 -pyrrolidone and to produce an intermediate heavies bottoms stream. In a further embodiment, the third overhead product stream is recycled to the heavies fractionation zone.

DETAILED DESCRIPTION OF THE INVENTION

Figure 1:
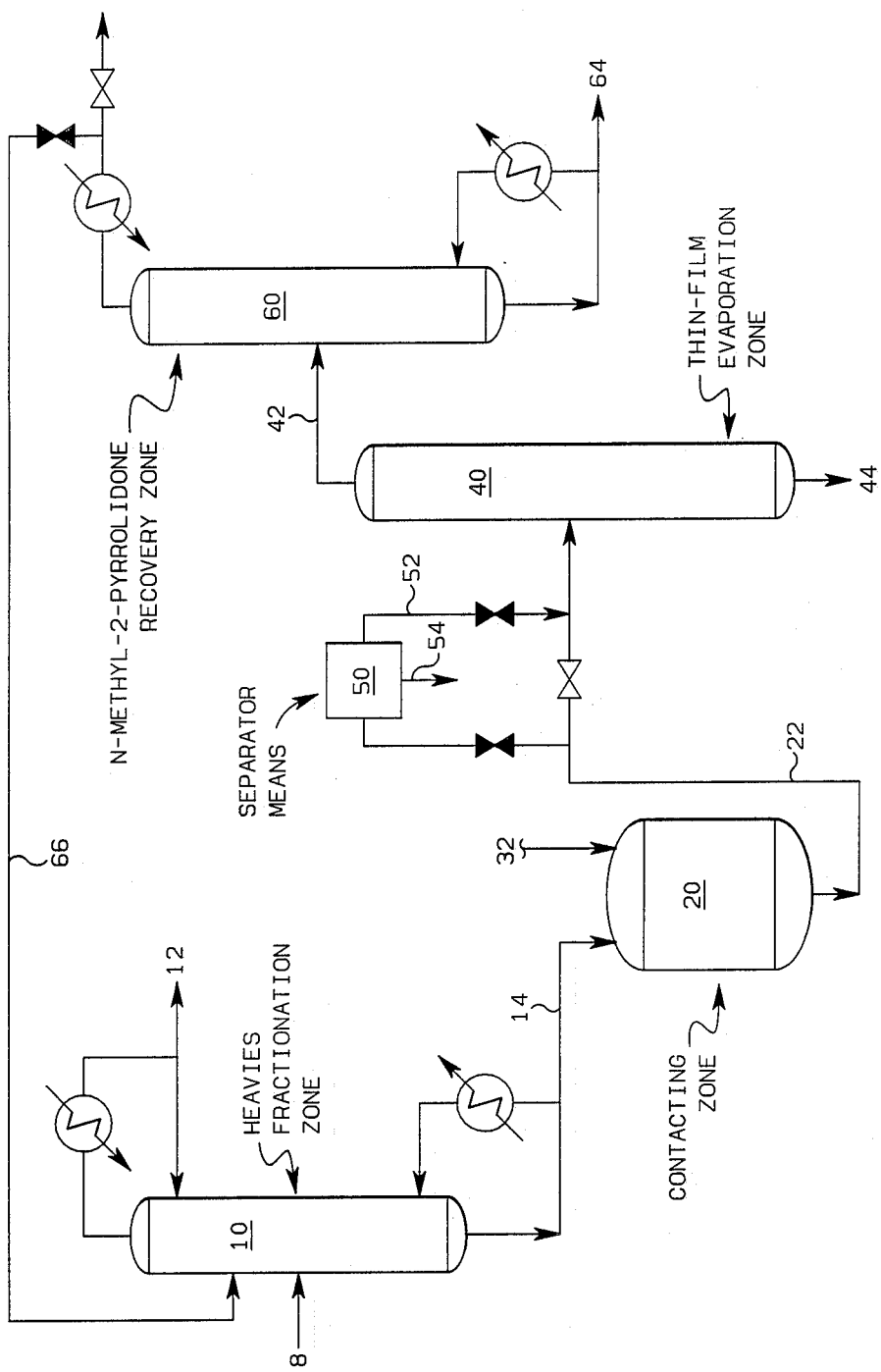
FIG. 1 is a schematic diagram illustrating a process for recovering N-methyl-2-pyrrolidone utilizing a thin-film evaporator and fractionation of the thin-film evaporator overhead product in an N-methyl-2-pyrrolidone recovery zone with optional recycle of the NMP recovery zone overhead product to a heavies fractionation zone.
Figure 2:
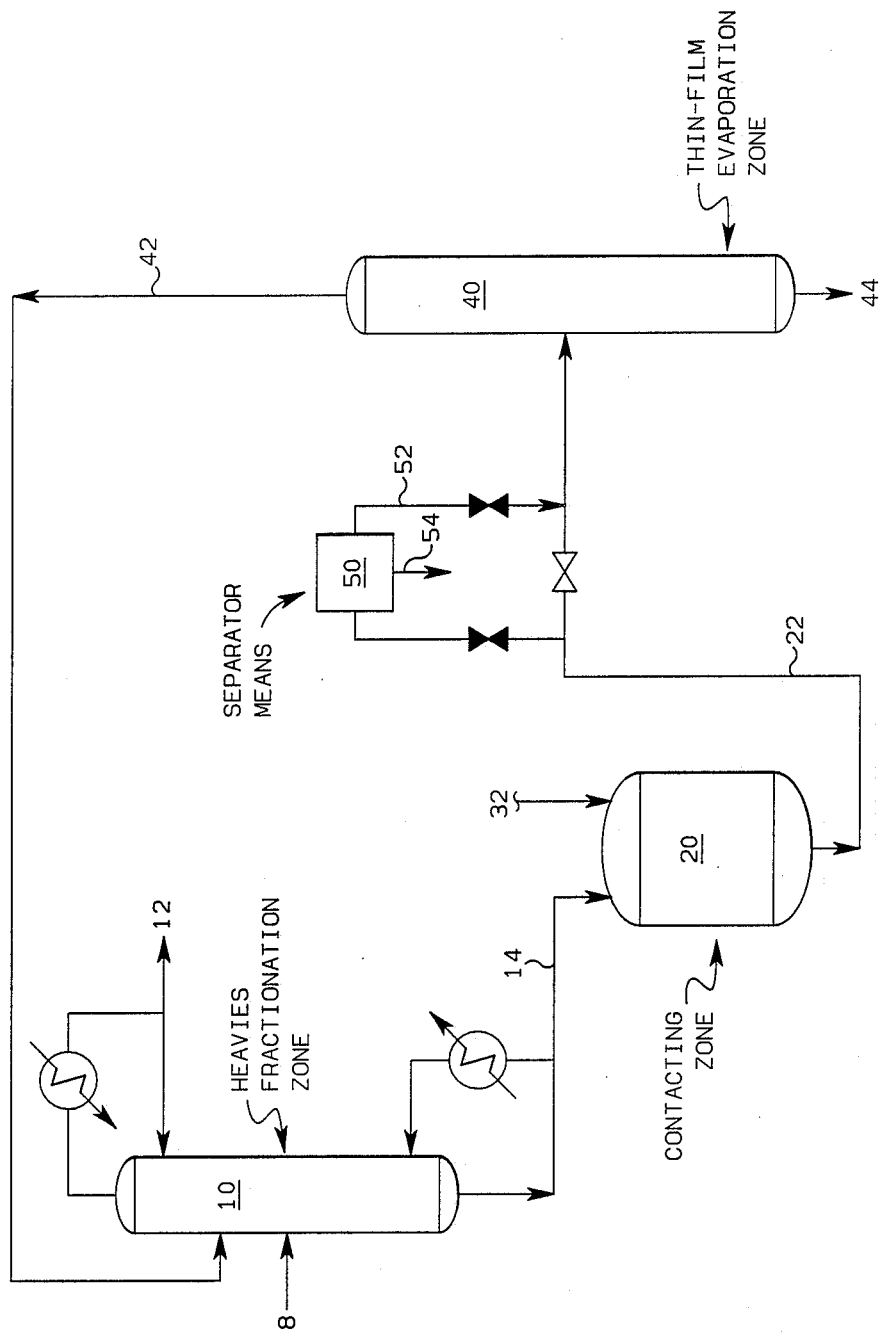
FIG. 2 is a schematic diagram illustrating a process for recovering N-methyl-2-pyrrolidone utilizing a thin-film evaporator with recycle of the thin-film evaporator overhead product to a heavies fractionation zone.
Figure 1:
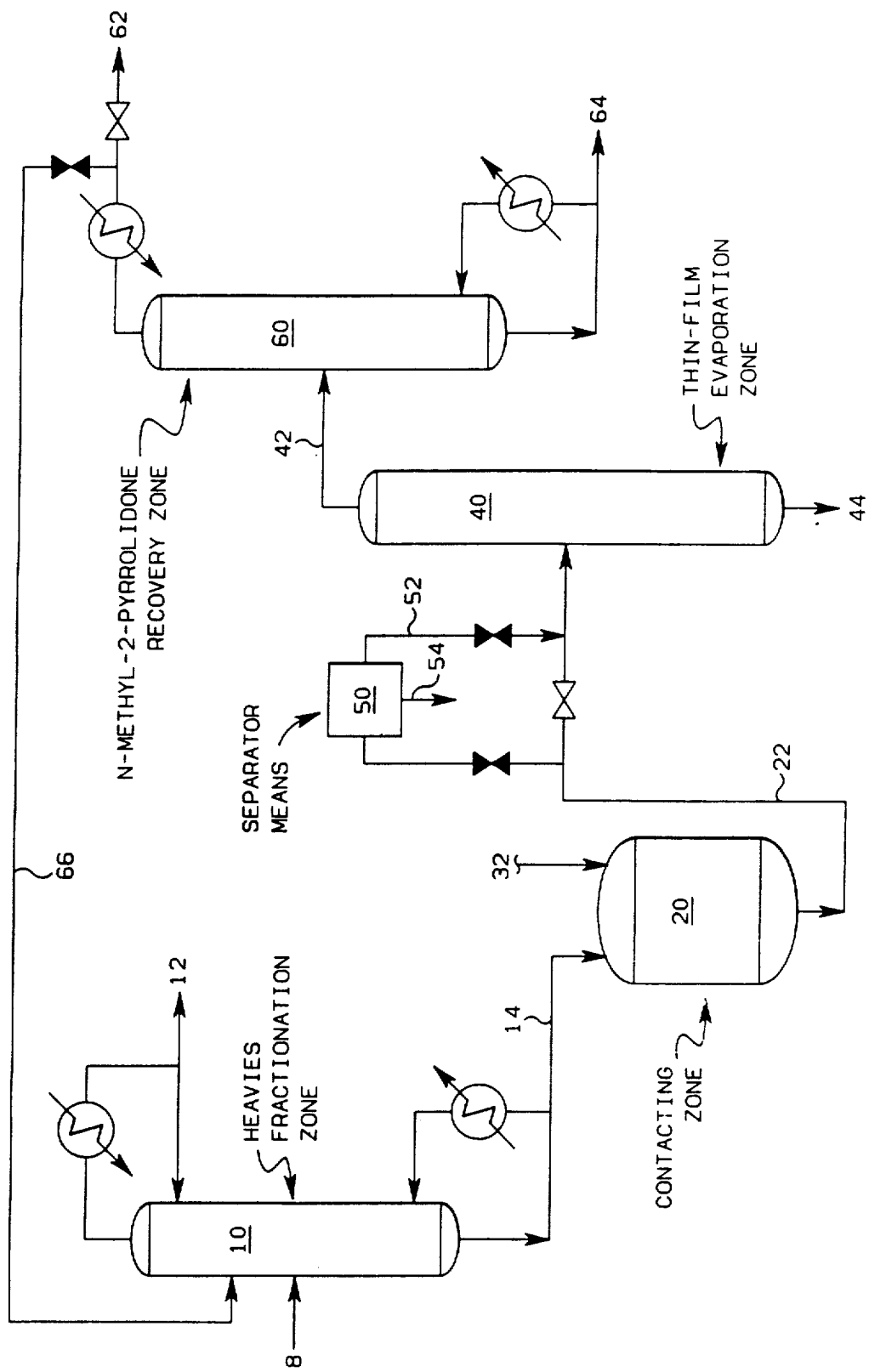
Figure 2:
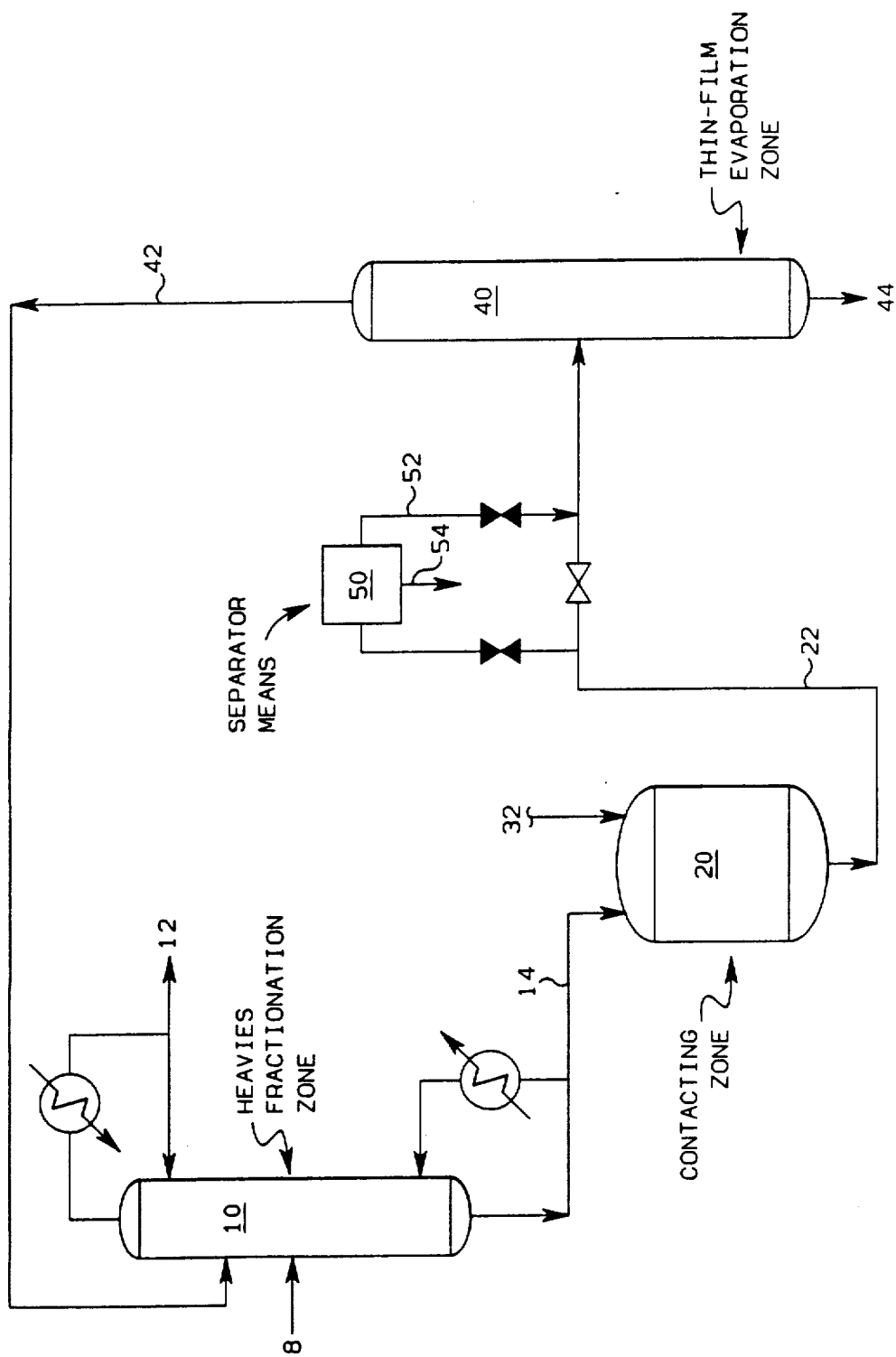

The recovery of N-methyl-2-pyrrolidone from an effluent stream in a poly(arylene sulfide) process, as illustrated in FIGS. 1 and 2, comprises passing an eiiluent stream 8 containing NMP contaminated with acidic compounds and high boiling contaminants to a heavies fractionation zone 10 and fractionating effluent stream 8 to produce a first overhead product stream 12 containing N-methyl-2-pyrrolidone and a kettle liquid 14 containing the remaining N-methyl-2-pyrrolidone, acidic compounds and high boiling contaminants, contacting in a contacting zone 20 the kettle liquid 14 with an inorganic compound 32 in an amount effective to reduce the acidic compound content of the kettle liquid 14 to produce a treated kettle liquid 22, and introducing the treated kettle liquid 22 into a thin-film evaporation zone 40 and evaporating to produce a second overhead product stream 42 containing N-methyl-2-pyrrolidone and a bottoms stream 44 containing N-methyl-2-pyrrolidone soluble reaction products of the acidic compounds with the inorgainc compound, unreacted acidic compounds, and high boiling contaminants.

Applicable inorganic compounds are those selected from the group consisting of alkaline earth oxides and alkaline earth hydroxides. The preferred alkaline earth oxide is calcium oxide and the preferred alkaline earth hydroxide is calcium hydroxide. The preferred inorganic compound is calcium oxide due to its effectiveness in reducing the acidic compound content. The level of inorganic compound used to treat the kettle liquid containing N-methyl-2-pyrrolidone, acidic compounds and high boiling contaminants can be based on the level of the major acidic compound, i.e. phenol, present in the kettle liquid. The mole ratio of inorganic compound to the major acidic compound is from about 1 to about 10, preferably from 1 to 5, and most preferably from 1 to 2. Alternately, the level of inorganic compound can be based on the total amount of the kettle liquid to be treated. The ratio of pounds of kettle liquid to be treated to pound moles of inorganic compound is from about 60 to about 600, preferably from about 120 to about 600, and most preferably from about 300 to about 600.

The means of contact of the kettle liquid with the inorganic compound in contacting zone 20 can be chosen from such processes as stirred slurry contact of the solid inorganic compound with the kettle liquid, fluidized bed contact of the kettle liquid with solid inorganic compound, or trickle bed contact of the kettle liquid passing through a bed of solid inorganic compound. The contact can be made at room temperature or at an elevated temperature up to the operating temperature of the heavies fractionation zone. An elevated temperature is preferred due to the effectiveness of acidic compound removal. The preferred contacting temperature range is from about 300F. to about 400F. The contacting is also preferably done under an inert atmosphere using an inert gas such as nitrogen to prevent oxidation of N-methyl-2-pyrrolidone. In the cases of fluidized bed contact and trickle bed contact, provision is made for removal of spent inorganic compound. This can be accomplished by having dual contactors for alternate use or means for withdrawing inorganic compound with replacement by fresh maierial on a continuous basis. The current preferred contacting method is stirred slurry contact due to operability advantages, particularly in view of the ability of the thin-film evaporator to handle solids.

The thin-film evaporator of the invention can be vertical or horizonial and are capable of handling materials that have a high solids content. Operation of the thin-film evaporator comprises spreading liquid on the heated evaporator wall using a rotating assembly of blades that either maintain a close clearance from the wall or actually ride on the film of liquid on the wall.

In a further embodiment, the treated kettle liquid 22 can optionally be passed through a separator means 50 to remove solids 54 prior to introducing the separator means product stream 52 into the thin-film evaporation zone 40. The solids removed from the separator means include any unreacted inorganic compound. The separator means applicable for use in the invention include any conventional means of liquid-solid separation, although a pressure filter or a vacuum filter is preferred.

In one embodiment of the invention, as illustrated in FIG. 1, the second overhead product stream 42 is introduced to an N-methyl-2-pyrrolidone recovery zone 60 and fractionated to produce a third overhead product stream 62 consisting essentially of N-methyl-2-pyrrolidone and an intermediate heavies bottom stream 64. In a further embodiment, the third overhead product stream 62 can optionally be recycled through line 66 to the heavies fractionation zone 10.

In another embodiment of the invention, as illustrated in FIG. 2, the second overhead product stream 42 of the thin-film evaporation zone 40 is recycled directly to the heavies fractionation zone 10.

EXAMPLE I

A 5-gallon sample of heavies fractionation zone kettle liquid was obtained from the commercial Phillips Petroleum Company Ryto TM poly(phenylene sulfide) plant and analyzed using gas chromatography. The untreated kettle liquid analysis (Run 1) was used as the control for tests where the kettle liquid was treated with an inorganic compound. All gas chromatography analyses of the samples in the examples were made with a Hewlett-Packard Model 5880A gas chromatograph equipped with a 25 meter Supelco Wax 20M fused silica capillary column with a film thickness of 0.25 microns. The contaminated N-methyl-2-pyrrolidone sample corresponds to the kettle liquid stream 14 of FIG. 1 and was found to be contaminated with various undesirable components such as phenol, 1,3-dimethylpyrrolidone, diphenylether and heavies.

A sample of the kettle liquid was treated by contacting with calcium oxide (Run 2). The apparatus used for the contacting consisted of a 2,000 mL wide-opening flask with a matching head containing four neck openings in which were mounted a reflux condenser, a nitrogen purge line, a thermometer and a thermocouple. The thermocouple was connected to a high temperature override on the variable electric heating controller. Heat was supplied to the bottom of the flask with a heating mantle. The contents of the flask were agitated using a magnetic stirring bar.

For Run 2, 700 mL (750 grams) of kettle liquid was charged to the flask, the flask assembled, and the contents heated to 390° F. while purging with nitrogen at 1 SCFH. When the temperature of the kettle reached 390° F., the nitrogen purge was reduced to 0.4 SCFH and 85.2 grams (1.52 moles) CaO was added with the temperature dropping to 375° F. The temperature was increased to 388° F. over the next 60 minutes at which time the power to the heating mantle was stopped and the treated kettle liquid allowed to cool. The sample was filtered and the filtrate analyzed using gas chromatography.

A sample of kettle liquid was treated by contacting with calcium hydroxide (Run 3) using the same apparatus as in Run 2. For Run 3, 700 mL (750 grams) of kettle liquid and 112.6 grams (1.52 moles) $Ca(OH)_2$ were charged to the flask, the flask assembled, and the contents purged with 1 SCFH of nitrogen. After one hour, the nitrogen purge was reduced to 0.4 SCFH and the contents heated to 356° F. in 18 minutes and maintained within 345°–356° F. for 60 minutes at which time the power to the heating mantle was stopped and the treated kettle liquid allowed to cool. The sample was filtered and the filtrate analyzed using gas chromatography.

A sample of kettle liquid was treated by contacting with calcium oxide (Run 4) using the same apparatus as in Run 2 except a 3,000 mL flask was used. For Run 4, 2225 grams kettle liquid and 299.3 grams (5.34 moles) CaO were charged to the flask, the flask assembled and the contents purged with 1.5 SCFH of nitrogen. After 40 minutes, the nitrogen purged was reduced to 0.4 SCFH and the contents heated to 401° F. in 40 minutes and maintained within 383°–401° F. for 35 minutes at which time the power to the heating mantle was stopped and the treated kettle liquid allowed to cool. A small portion of the sample was filtered and the filtrate analyzed using gas chromatography.

The results obtained are presented in Table I. The results in Table I indicate both calcium oxide and calcium hydroxide are effective at removing acidic compounds, e.g. phenol, from a kettle liquid sample. As can be seen from Runs 2 and 3, calcium oxide is more efecitve than calcium hydroxide. In addition, increasing the amount of calcium oxide results in increased removal of phenol as evidenced by Runs 2 and 4.

TABLE I

Treatment of Kettle Liquid by Stirred Slurry Contact

| | Run No. | | | |
|---|---|---|---|---|
| | 1[a] | 2 | 3 | 4 |
| Inorganic Compound | — | CaO | Ca(OH)$_2$ | CaO |
| Mole ratio, inorganic compound:phenol[b] | — | 1.25 | 1.25 | 1.48 |
| Analysis, wt. % | | | | |
| N-methyl-2-pyrrolidone | 73.51 | 76.19 | 78.5 | 84.13 |
| phenol | 15.27 | 6.89 | 9.69 | 4.34 |
| diphenyl ether | 1.3 | 1.5 | 1.36 | 0.8 |
| 1,3-dimethylpyrrolidone | 0.06 | 0.07 | 0.06 | 0.065 |
| N-methyl succinimide | ND[c] | ND[c] | ND[c] | 0.154 |
| heavies | 9.86 | 15.35 | 10.35 | 10.51 |
| lights | ND[c] | 0.01 | 0.03 | ND[c] |
| % phenol removed | — | 55 | 37 | 72 |

[a]original untreated kettle liquid sample.
[b]Mole ratio of inorganic compound to phenol present in kettle liquid sample.
[c]Not detected.

EXAMPLE II

The runs in Example 2 were ell runs in the flask apparatus described in Example I, Run 2. A synthetic N-methyl-2-pyrrolidone/ phenolmixture was treated with calcium oxide (Run 5). A 750 gram sample of the synthetic mixture containing 78.4 weight percent N-methyl-2-pyrrolidone and 21.6 weight percent phenol was charged to the flask with 96.5 grams (1.72 moles) CaO, the flask assembled and the contents purged with 1 SCFH of nitrogen. After one hour, the nitrogen purge was reduced to 0.4 SCFH and the contents heated to 367° F. in 20 minutes and maintained with 367°–390° F. for 40 minutes at which time the power to the heating mantle was stopped and the treated synthetic mixture allowed to cool. A small portion of the treated synthetic mixture gas filtered and the filtrate analyzed using gas chromatography. Upon addition of water to either the slurry or the filtrate, a white precipitate formed. To determine if the precipitate was a soluble calcium salt, the filtrate was sampled and a metals analysis was performed.

The gas chromatography results obtained are presented in Table II and the metals analysis results obtained are presented in Table III.

A sample of N-methyl-2-pyrrolidine was treated with calcium oxide (Run 6). A 750 gram sample of N-methyl-2-pyrrolidone and 96.5 grams (1.72 moles) CaO were charged to the flask, the flask assembled, and the contents purged with 1 SCFH of nitrogen. After one hour the nitrogen purge was reduced to 0.4 SCFH and the contents heated to 351° F. in 21 minutes and maintained within 351°–379° F. for 48 minutes at which time the power to the heating mantle was stopped and the treated N-methyl-2-pyrrolidone allowed to cool. The treated N-methyl-2-pyrrolidone sample was filtered and upon addition of water to either the slurry or the filtrate no precipitate formed. The recovered solids were dried and 98 grams of material was obtained. It is unknown why an additional 1.5 grams of solids were recovered.

A phenol/water mixture was treated with calcium oxide (Run 7) by charging 162 grams (1.72 moles) phenol, 588 grams (32.7 moles) water and 96.5 grams (1.72 moles) CaO to the flask and the flask assembled. The slurry immediately turned a brownish color upon addition of the calcium oxide and an exotherm was observed as the temperature rose from 77° F. to 138° F. within 8 minutes. The flask contents were heated to 194° F. in 24 minutes and maintained within 194°–212° F. for 53 minutes at which time the power to the heating mantle was stopped and the slurry allowed to cool. The slurry was filtered and the solids recovered and dried.

The solids recovered from Run 7 were charged to the flask with 588 grams (5.94 moles) N-methyl-2-pyrrolidone (Run 8), the flask assembled, and the contents purged with 1 SCFH of nitrogen. After one hour the nitrogen purge was reduced to 0.4 SCFH and the contents heated to 372° F. in 20 minutes and maintained at 372°–387° F. for 40 minutes at which time the power to the heating mantle was stopped and the contents allowed to cool. A portion of the contents were filtered and both the slurry and the filtrate produced a precipitate upon addition of water.

The effectiveness of calcium oxide in removing phenol is again demonstrated in Table II. It is clear from the results of Table III that the white precipitate is some type of soluble calcium salt formed during the treatment. The results of Run 6 indicate that no soluble salt is produced by contacting N-methyl-2-pyrrolidone with calcium oxide. The results of Runs 7 and 8 indicate that a calcium salt of phenol and calcium oxide is formed and that this salt is soluble in N-methyl-2-pyrrolidone. The formation of this soluble salt necessitates a process for recovering N-methyl-2-pyrrolidone which is capable of handling solids without fouling.

TABLE II

Treatment of Synthetic Mixture by Stirred Slurry Contact

| | Run No. 5 |
|---|---|
| Inorganic Compound | CaO |
| Mole Ratio, inorganic compound:phenol | 1.0 |
| Analysis. wt. % | |
| N-methyl-2-pyrrolidone | 95.18 |
| phenol | 4.63 |
| 1,3-dimethylpyrrolidone | 0.01 |
| heavies | 0.15 |
| lights | 0.03 |
| % phenol removed | 79 |

TABLE III

Metals Analysis of Run 5 Filtrate[a]

| Metal | Concentration |
|---|---|
| Calcium | 4.9 wt. % |
| Chromium | 620 ppb |
| Iron | 7.76 ppm |
| Magnesium | 4.01 ppm |
| Molybdenum | 510 ppb |
| Sodium | 27.9 ppm |
| Strontium | 12.1 ppm |
| Titanium | 17.8 ppm |
| Zinc | 8.81 ppm |
| Barium | 360 ppb |

[a]Metals analysis was done by plasma emission using an Applied Research Laboratories (ARL) Model ICPQ 1-37000.

EXAMPLE III

An 1,151.1 gram sample of the calcium oxide treated kettle liquid from Run 4 was charged to a 2,000 mL flask and connected to a variable speed rotary vacuum evaporator with stationary diagonal condenser. The rotating 2,000 mL flask was placed in an oil bath for temperature control and a vacuum of 27.5 in. Hg was pulled on the rotary vacuum evaporator. The oil bath temperature was slowly raised to 300° F. and a 641.4 gram first cut of overhead product was taken and sampled for gas chromatography analysis. The oil bath was then treated to 335° F., and a 40.2 gram second cut of overhead product was taken and sampled for gas chromatography analysis.

The results obtained are presented in Table IV. The results in Table IV indicate that 84 percent of the N-methyl-2-pyrrolidone was recovered using a simple rotary vacuum evaporator. Therefore, a more efficient thin-film evaporator would be effective in an N-methyl-2-pyrrolidone recovery process where a soluble salt is present in the treated kettle liquid.

TABLE IV

Rotary Vacuum Evaporation of CaO Treated Kettle Liquid

| Component | Analysis, wt. % | |
|---|---|---|
| | First Cut | Second Cut |
| N-methyl-2-pyrrolidone | 95.97 | 60.95 |
| phenol | 0.26 | 1.49 |
| diphenyl ether | 0.58 | 4.28 |
| 1,3-dimethylpyrrolidone | 0.077 | 0.029 |
| N-methylsuccinimide | 0.021 | 0.033 |
| heavies | 3.09 | 33.21 |
| % N-methyl-2-pyrrolidone recovered | 81 | 3 |

That which is claimed is:

1. A process for recovery of N-methyl-2-pyrrolidone from an effluent stream in a poly(arylene sulfide) process wherein said effluent stream contains said N-methyl-2-pyrrolidone contaminated with acidic compounds and high boiling contaminants comprising:
   (a) passing said effluent stream to a heavies fractionation zone and fractionating said effluent stream to produce a first overhead product stream containing N-methyl-2-pyrrolidone and a kettle liquid containing the remaining N-methyl-2-pyrrolidone, acidic compounds and high boiling contaminants,
   (b) contacting said kettle liquid with an inorganic compound selected from the group consisting of alkaline earth oxides and alkaline earth hydroxides in an amount effective to reduce the acidic compound content of said kettle liquid, and
   (c) introducing ihe thus treated kettle liquid into a thin-film evaporation zone and evaporating to produce a second overhead product stream containing N-methyl-2-pyrrolidone and a bottoms stream containing reaction products of said acidic compounds with said inorganic compound which are soluble in N-methyl-2-pyrrolidone, unreacted said acidic compounds, and said high boiling contaminants.

2. A process according to claim 1 further comprising introducing said second overhead product stream to an N-methyl-2-pyrrolidone recovery zone and fractionating to produce a third overhead product stream consisting essentially of N-methyl-2-pyrrolidone and an intermediate heavies bottom stream.

3. A process according to claim 1 wherein said contacting of said kettle liquid with said inorganic compound is conducted by a process of stirred slurry contact of said kettle liquid with said inorganic compound.

4. A process according to claim 1 wherein said contacting of said kettle liquid with said inorganic compound is conducted by a process of fluidized bed contact of said kettle liquid with solid inorganic compound.

5. A process according to claim 1 wherein said contacting of said kettle liquid with said inorganic compound is conducted by a process of trickle bed contact of said kettle liquid with solid inorganic compound.

6. A process according to claim 3 wherein said treated kettle liquid is passed through a separator means to remove solids prior to introducing said treated kettle liquid into said thin-film evaporation zone.

7. A process according to claim 6 wherein said solids include unreacted inorganic compound.

8. A process according to claim 7 wherein said inorganic compound is calcium oxide.

9. A process according to claim 4 wherein said inorganic compound is calcium oxide.

10. A process according to claim 5 wherein said inorganic compound is calcium oxide.

11. A process according to claim 1 wherein said second overhead product stream of said thin-film evaporation zone is recycled to said heavies fractionation zone.

12. A process according to claim 11 wherein said contacting of said kettle liquid with said inorganic compound is conducted by a process of stirred slurry contact of said kettle liquid with said inorganic compound.

13. A process according to claim 11 wherein said contacting of said kettle liquid with said inorganic compound is conducted by a process of fluidized bed contact of said kettle liquid with solid inorganic compound.

14. A process according to claim 11 wherein said contacting of said kettle liquid with said inorganic compound is conducted by a process of trickle bed contact of said kettle liquid with solid inorganic compound.

15. A process according to claim 12 wherein said treated kettle liquid is passed through a separator means to remove solids prior to introducing said treated kettle liquid into said thin-film evaporation zone.

16. A process according to claim 15 wherein said solids include unreacted inorganic compound.

17. A process according to claim 16 wherein said inorganic compound is calcium oxide.

18. A process according to claim 13 wherein said inorganic compound is calcium oxide.

19. A process according to claim 14 wherein said inorganic compound is calcium oxide.

20. A process according to claim 2 further comprising recycling said third overhead product stream to said heavies fractionation zone.

21. A process according to claim 20 wherein said contacting of said kettle liquid with said inorganic compound is conducted by a process of stirred slurry contact of said kettle liquid with said inorganic compound.

22. A process according to claim 20 wherein said contacting of said kettle liquid with said inorganic compound is conducted by a process of fluidized bed contact of said kettle liquid with solid inorganic compound.

23. A process according to claim 20 wherein said contacting of said kettle liquid with said inorganic compound is conducted by a process of trickle bed contact of said kettle liquid with solid inorganic compound.

24. A process according to claim 21 wherein said treated kettle liquid is passed through a separator means to remove solids prior to introducing said treated kettle liquid into said thin-film evaporation zone.

25. A process according to claim 24 wherein said solids include unreacted inorganic compound.

26. A process according to claim 25 wherein said inorganic compound is calcium oxide.

27. A process according to claim 22 wherein said inorganic compound is calcium oxide.

28. A process according to claim 23 wherein said inorganic compound is calcium oxide.

29. A process for recovery of N-methyl-2-pyrrolidone from an effluent stream in a poly(arylene sulfide) process wherein said effluent stream contains said N-methyl-2-pyrrolidone contaminaied with acidic compounds and high boiling contaminants comprising:

(a) passing said effluent stream to a heavies fractionation zone and fractionating said effluent stream to produce a first overhead product stream containing N-methyl-2-pyrrolidone and a kettle liquid containing the remaining N-methyl-2-pyrrolidone, acidic compounds and high boiling contaminants, (b) contacting said kettle liquid with calcium oxide in an amount effective to reduce the acidic compound content of said kettle liquid wherein said contacting is conducted by stirred slurry contact of said kettle liquid with said calcium oxide, (c) introducing the thus treated kettle liquid into a thin-film evaporation zone and evaporating to produce a second overhead product stream containing N-methyl-2-pyrrolidone and a bottoms stream containing reaction products of said acidic compounds with said calcium oxide which are soluble in N-methyl-2-pyrrolidone, unreacted said acidic compounds, unreacted calcium oxide and said high boiling contaminants, and (d) recycling said second overhead product stream of said thin-film evaporation zone to said heavies fractionation zone.

* * * * *

UNITED STATES PATENT AND TRADEMARK OFFICE
CERTIFICATE OF CORRECTION

PATENT NO. : 4,965,370

DATED : October 23, 1990

INVENTOR(S) : Kenneth D. Goetz and Bradley L. Munro

It is certified that error appears in the above-identified patent and that said Letters Patent is hereby corrected as shown below:

Page 1, Assignee, please delete "Phillips Friedman Company" and insert therefor ---Phillips Petroleum Company---.

Column 7, line 47, please delete "ihe" and insert therefor ---the---.

Column 9, line 14, please delete "contaminaied" and insert therefor ---contaminated---.

Signed and Sealed this

Tenth Day of March, 1992

Attest:

HARRY F. MANBECK, JR.

Attesting Officer          Commissioner of Patents and Trademarks

UNITED STATES PATENT AND TRADEMARK OFFICE
CERTIFICATE OF CORRECTION

PATENT NO. : 4,965,370

DATED : October 23, 1990

INVENTOR(S) : Bradley L. Munro and Kenneth D. Goetz

It is certified that error appears in the above-identified patent and that said Letters Patent is hereby corrected as shown below:

The sheets of drawings consisting of Figs. 1-2, should be added as shown on the attached pages.

Signed and Sealed this

Twenty-first Day of April, 1992

Attest:

HARRY F. MANBECK, JR.

Attesting Officer

Commissioner of Patents and Trademarks